United States Patent [19]

Hollenberg et al.

[11] Patent Number: 5,779,860
[45] Date of Patent: Jul. 14, 1998

[54] HIGH-DENSITY ABSORBENT STRUCTURE

[75] Inventors: David Henry Hollenberg, Kaukauna; James Ellis Horton, Jr., Appleton; Andrew Michael Lake, Combined Locks, all of Wis.

[73] Assignee: Kimberly-Clark Worldwide, Inc., Neenah, Wis.

[21] Appl. No.: 773,797

[22] Filed: Dec. 17, 1996

[51] Int. Cl.$^6$ ............................................. D21F 11/00
[52] U.S. Cl. ................................. 162/206; 264/280
[58] Field of Search ........................... 264/280; 162/206

[56] References Cited

U.S. PATENT DOCUMENTS

| | | | |
|---|---|---|---|
| 3,556,932 | 1/1971 | Coscia et al. | 162/166 |
| 3,556,933 | 1/1971 | Williams et al. | 162/167 |
| 3,700,623 | 10/1972 | Keim | 260/80.3 R |
| 3,772,076 | 11/1973 | Keim | 117/155 R |
| 3,855,158 | 12/1974 | Petrovich et al. | 260/2 BP |
| 3,899,388 | 8/1975 | Petrovich et al. | 162/164 |
| 4,129,528 | 12/1978 | Petrovich et al. | 260/823 |
| 4,147,586 | 4/1979 | Petrovich et al. | 162/135 |
| 4,222,921 | 9/1980 | Van Eenam | 260/29.6 H |
| 4,675,394 | 6/1987 | Solarek et al. | 536/43 |
| 4,981,557 | 1/1991 | Bjorkquist | 162/168.2 |
| 5,008,344 | 4/1991 | Bjorkquist | 525/328.2 |
| 5,069,548 | 12/1991 | Boehnlein | 356/376 |
| 5,085,736 | 2/1992 | Bjorkquist | 162/168.2 |
| 5,324,575 | 6/1994 | Sultze et al. | 428/224 |
| 5,399,412 | 3/1995 | Sudall et al. | 428/153 |
| 5,429,686 | 7/1995 | Chiu et al. | 139/383 A |

FOREIGN PATENT DOCUMENTS

| | | |
|---|---|---|
| 3-185197 A | 8/1991 | Japan |
| WO 96/09435 A1 | 3/1996 | WIPO |

OTHER PUBLICATIONS

Bieman, L. H., K. G. Harding, and A. Boehnlein, "Absolute Measurement Using Field Shifted Moire," *SPIE Optical Conference Proceedings*, vol. 1614, Nov. 14–15, 1991, pp. 259–264.

Mummery, Leigh, *Surface Texture Analysis: The Handbook*, published by Hommelwerke GmbH, Muhlhausen, Germany, 1990, pp. 28–29.

*Primary Examiner*—James J. Bell
*Attorney, Agent, or Firm*—Gregory E. Croft

[57] ABSTRACT

Low-density uncreped through-air-dried webs containing bleached chemithermomechanical pulp fibers and a wet-strength resin are calendered to significantly increase density and reduce caliper. When wetted, these webs substantially return to their original caliper and density and substantially regain their original fluid-handling characteristics. Consequently these webs are very thin when dry and thick when wet. They can be used for a wide variety of applications, including paper towels, wipers and fluid-handling components for infant care and personal care products.

11 Claims, 4 Drawing Sheets

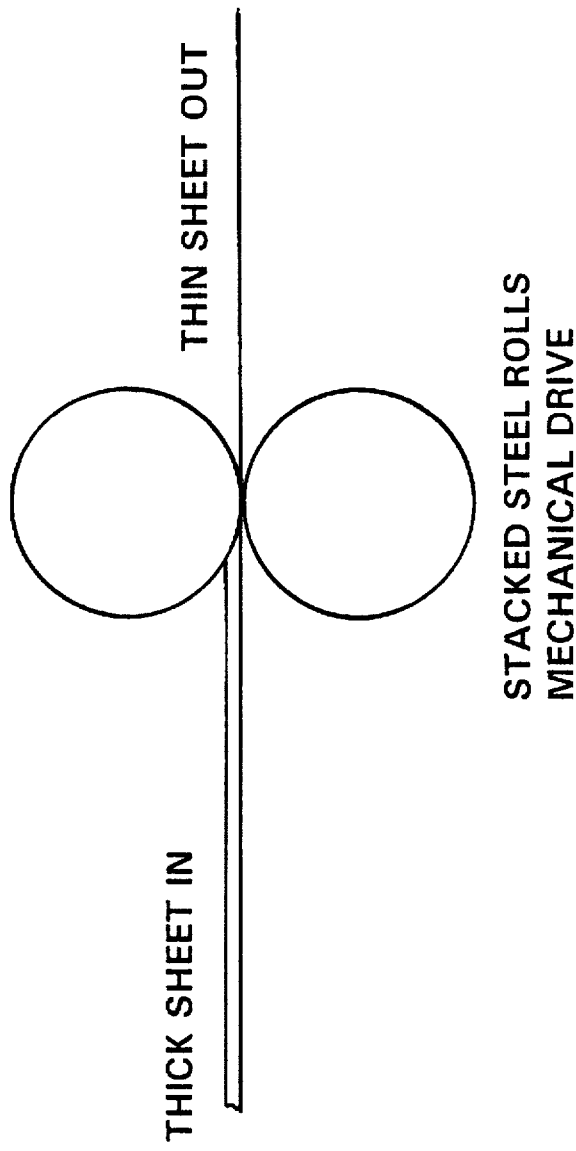

Surface depth from a two-dimensional height profile of a surface with 4 repeating elements.

Surface depth from a two-dimensional height profile of a surface with 5 repeating but variable height elements.

HIGH-DENSITY ABSORBENT STRUCTURE

BACKGROUND OF THE INVENTION

In the manufacture of fiber-based materials used to absorb and contain fluids such as water, milk, coffee or urine, nasal discharge and other body exudates, it is commonly a property of the absorbent materials that they have a low density and corresponding high void volume. The high void volume allows for absorption and containment of the fluid, but leads to products that have a low overall density and occupy substantial volume. This inherent void volume is a characteristic of absorbent materials in that the fluid to be contained needs to reside in most cases in the void volume of the fiber web. Heretofore, most materials currently used in products designed to absorb and contain fluid, while having large void volumes, are inherently low in density and are therefore bulky.

The low density of the materials, while providing the desired performance in the product, also imposes some penalties in the form of bulky, low-density products. For the producer of products, the low density of the absorbent materials imparts a penalty in packaging and transporting of its products. For the converter, it imposes problems in storage, handling and shipping of its final products. For the retailer, it means using a large amount of shelf space for a relatively small number of products. For the ultimate consumer, it means handling, storing and using bulky, low-density materials. For such products as diapers, feminine pads and tissue and towel products, the functionality of the products as absorbents generally outweighs the disadvantages of the bulk imposed by the low density; however, given a choice, most consumers would prefer to have thinner, less bulky products. While the advantages to the consumer are obvious, there are many other advantages that thin, dense, but highly absorbent materials can provide to product design, performance and consumer appeal.

SUMMARY OF THE INVENTION

The present invention pertains to materials that are relatively high in density and are not bulky in the dry state, but when exposed to aqueous fluids such as water, coffee and milk and body fluids, such as blood, urine, nasal discharge and other body exudates, swell and increase their void volume to accommodate and contain the fluids. Such thin, dense materials should find application in the design of new, nonbulky consumer items. These materials could also form the basis for new and improved products used to contain fluids in the commercial and professional product areas.

In copending patent appliction Ser. No. 08/310,186 to Chen et al. filed Sep. 21, 1994, a low-density, wet-laid tissue sheet with exceptional wet resilience and absorbency was disclosed. One of the desirable attributes of this material is the resistance of its structure to collapse when the sheet is saturated with fluid. This attribute of wet collapse resistance imparts a significant improvement in fluid handling properties to these fiber webs. Their low density and ability to retain their low density when saturated with fluid is unique. These materials are finding wide use in developing consumer products for absorbent purposes. These materials are being used as components of diapers, bed pads and feminine hygiene products in addition to their application in the more traditional tissue and towel applications.

It has been found that the materials of this previous invention and similar wet-resilient structures can be compressed under suitable conditions to provide materials of relatively high density that retain their fluid handling and absorbing properties. When exposed to aqueous solutions and fluids, these materials expand and produce internal voids that can absorb and hold fluid. This property is especially useful in making absorbent materials that are thin when dry, but swell when wetted and are capable of holding large volumes of fluid. The swelling associated with exposure to fluids is largely the resumption of the original low-density structure. By using basesheets that have this property of wet collapse resistance, subsequent compression provides materials that are thin when dry but become thick when wet.

There are a number of applications for this compressed material in absorbent products. Incorporation of these materials in diapers, feminine hygiene products, and in other absorbent media is of particular value as these structures have been shown to efficiently absorb most types of fluids these products are normally expected to absorb and contain. In addition, towel and tissue products made from these compressed products retain their fluid handling properties but are less bulky and tend to be perceived as softer and more comfortable than conventional, non-compressed materials.

Hence, in one aspect, the invention resides in an absorbent structure comprising high yield pulp fibers having a wet:dry geometric mean tensile ratio of about 0.1 or greater, a density of about 0.3 grams per cubic centimeter or greater and an absorbent capacity of about 4 grams of water per gram of fiber or greater.

More specifically, the invention resides in a compressed uncreped through-air-dried web of papermaking fibers comprising high yield pulp fibers and a wet strength agent, said web having a density of about 0.3 grams per cubic centimeter or greater and an absorbent capacity of about 4 grams of water per gram of fiber.

In another aspect, the invention resides in a method of making an absorbent structure comprising: (a) forming a structure having a density of about 0.2 grams per cubic centimeter or less, said structure comprising high yield pulp fibers and having a wet:dry geometric mean tensile ratio of about 0.1 or greater and (b) compressing the structure to increase its density to about 0.3 grams per cubic centimeter or greater, wherein upon being saturated with distilled water, the density decreases about 20 percent or greater.

More specifically, the invention resides in a method of making an absorbent structure comprising: (a) forming an uncreped through-air-dried web comprising high yield pulp fibers and having a wet:dry geometric mean tensile ratio of about 0.1 or greater, and (b) calendering the web to increase its density to about 0.3 grams per cubic centimeter or greater, wherein upon being saturated with distilled water, the density decreases about 20 percent or greater.

In carrying out the method of this invention, compression of the relatively low-density sheet can be carried out by a number of methods. In the paper industry, it is well known that passing sheets through one or more rollers or nips will help compress and smoothen the surfaces of materials. The equipment used to do this is termed a calender or supercalender. The effect of calendering on low density sheets used in this invention depends upon the temperature, the pressure applied and the duration of the pressure. For purposes herein, calendering can be carried out at either at ambient or elevated temperatures. Suitable calendering pressures can be from about 50 to about 1400 pounds per linear inch (pli). Suitable temperatures can be from about 20° C. to about 240° C. The duration of calendering can be varied in conjunction with the nip pressure to produce the desired Caliper for the sheet.

In addition to calendering or supercalendering of the low density webs, the webs can be compressed using flat platten presses or fabric nips used to smooth and compact multi-wiper products as disclosed in U.S. Pat. No. 5,399,412 to Sudall et al. In this instance, the multi-ply wiper is carried on fabrics through a nip and the overall caliper of the multi-ply product is reduced. A similar process can be used to produce the sheets of the present invention. By inducing a pattern in the fabric or fabrics, the resulting sheet could have areas that are highly compressed and areas that are less compressed. The response of the resulting sheet to fluids would result in a regain of bulk, more or less uniformly, for the entire sheet.

Fibers useful for making the relatively low density sheets useful for purposes of this invention are wet resilient fibers that include high yield pulp fibers (further discussed below), flax, milkweed, abaca, hemp, cotton or any of the like that are naturally wet resilient or any wood pulp fibers that are chemically or physically modified, e.g. crosslinked or curled, that have the capability to recover after deformation in the wet state, as opposed to non-resilient fibers which remain deformed and do not recover after deformation in the wet state. Wet-resistant bonds are fiber-to-fiber bond sites that are resistant to disruption in the wet state resulting in a geometric mean wet tensile strength:geometric mean dry tensile strength ratio of 0.1 or greater.

As used herein, "high yield pulp fibers" are those paper-making fibers produced by pulping processes providing a yield of about 65 percent or greater, more specifically about 75 percent or greater, and still more specifically from about 75 to about 95 percent. Such pulping processes include bleached chemithermomechanical pulp (BCTMP), chemithermomechanical pulp (CTMP) pressure/pressure thermomechanical pulp (PTMP), thermomechanical pulp (TMP), thermomechanical chemical pulp (TMCP), high yield sulphite pulps, and high yield kraft pulps, all of which leave the resulting fibers with high levels of lignin. The preferred high yield pulp fibers are characterized by being comprised of comparatively whole, relatively undamaged tracheids, high freeness (over 250 CSF), and low fines content (less than 25 percent by the Britt jar test).

The amount of high yield pulp fibers in the relatively low density sheet can be at least about 10 dry weight percent or greater, more specifically about 30 dry weight percent or greater, still more specifically about 50 dry weight percent or greater, and up to 100 percent. For layered sheets, these same amounts can be applied to one or more of the individual layers. Because high yield pulp fibers are generally less soft than other papermaking fibers, it is advantageous to incorporate them into the middle of the final product, such as placing them in the center layer of a three-layered sheet or, in the case of a two-ply product, placing them in the inwardly-facing layers of each of the two plies.

Prior to compression, the low density sheets useful for purposes of this invention have a density of about 0.3 gram per cubic centimeter or less, more specifically about 0.15 gram or less, still more specifically about 0.1 gram per cubic centimeter or less. It is believed to be important that these relatively low density sheets, once formed, be dried without substantially reducing the number of wet-resilient interfiber bonds. Throughdrying, which is a common method for drying tissues and towels, is a preferred method of preserving the structure.

An integral part of the relatively low density sheets used for purposes of this invention is the material used to immobilize the bonds between the fibers in the wet state. Typically the means by which fibers are held together in paper and tissue products involve hydrogen and sometimes combinations of hydrogen bonds and covalent and/or ionic bonds. It is important to provide a material that will allow bonding of fibers in such a way as to immobilize the fiber-to-fiber bond points and make them resistant to disruption in the wet state. In this instance the wet state usually will mean when the product is exposed to water or other aqueous solutions, but could also mean exposure to body fluids such as urine, blood, mucus, menses, lymph and other body exudates.

There are a number of materials commonly used in the paper industry to impart wet strength to paper and board that are applicable to this invention. These materials are known in the art as wet strength agents and are commercially available from a wide variety of sources. Any material that when added to a paper or tissue results in providing a tissue or paper with a wet strength:dry strength ratio in excess of 0.1 will, for purposes of this invention, be termed a wet strength agent. Typically these materials are termed either as permanent wet strength agents or as "temporary" wet strength agents. For the purposes of differentiating permanent from temporary wet strength, permanent will be defined as those resins which, when incorporated into paper or tissue products, will provide a product that retains more than 50% of its original wet strength after exposure to water for a period of at least five minutes. Temporary wet strength agents are those which show less than 50% of their original wet strength after exposure to water for five minutes. Both classes of material find application in the present invention. The amount of wet strength agent added to the pulp fibers can be at least about 0.1 dry weight percent, more specifically about 0.2 dry weight percent or greater, and still more specifically from about 0.1 to about 3 dry weight percent based on the dry weight of the fibers.

Permanent wet strength agents will provide a more or less long-term wet resilience to the structure. This type of structure would find application in products that would require long-term wet resilience such as in paper towels and in many absorbent consumer products. In contrast, the temporary wet strength agents would provide structures that had low density and high resilience, but would not provide a structure that had long-term resistance to exposure to water or body fluids. While the structure would have good integrity initially, after a period of time the structure would begin to lose its wet resilience. This property can be used to some advantage in providing materials that are highly absorbent when initially wet, but which after a period of time lose their integrity. This property could be used in providing "flushable" products. The mechanism by which the wet strength is generated has little influence on the products of this invention as long as the essential property of generating water-resistant bonding at the fiber/fiber bond points is obtained.

The permanent wet strength agents that are of utility in the present invention are typically water soluble, cationic oligomeric or polymeric resins that are capable of either crosslinking with themselves (homocrosslinking) or with the cellulose or other constituent of the wood fiber. The most widely-used materials for this purpose are the class of polymer known as polyamide-polyamine-epichlorohydrin (PAE) type resins. These materials have been described in patents issued to Keim (U.S. Pat. Nos. 3,700,623 and 3,772,076) and are sold by Hercules, Inc., Wilmington, Del., as Kymene 557H. Related materials are marketed by Henkel Chemical Co., Charlotte, N.C. and Georgia-Pacific Resins, Inc., Atlanta, Ga.

Polyamide-epichlorohydrin resins are also useful as bonding resins in this invention. Materials developed by Monsanto and marketed under the Santo Res label are base-activated polyamide-epichlorohydrin resins that can be used in the present invention. These materials are described in patents issued to Petrovich (U.S. Pat. No. 3,855,158; U.S. Pat. No. 3,899,388; U.S. Pat. No. 4,129,528 and U.S. Pat. No. 4,147,586) and van Eenam (U.S. Pat. No. 4,222,921). Although they are not as commonly used in consumer products, polyethylenimine resins are also suitable for immobilizing the bond points in the products of this invention. Other classes of permanent-type wet strength agents are exemplified by the aminoplast resins obtained by reaction of formaldehyde with melamine or urea.

The temporary wet strength resins that can be used in connection with this invention include, but are not limited to, those resins that have been developed by American Cyanamid and are marketed under the name Parez 631 NC (now available from Cytec Industries, West Paterson, N.J. This and similar resins are described in U.S. Pat. Nos. 3,556,932 to Coscia et al. and 3,556,933 to Williams et al. Other temporary wet strength agents that should find application in this invention include modified starches such as those available from National Starch and marketed as Co-Bond 1000. It is believed that these and related starches are covered by U.S. Pat. No. 4,675,394 to Solarek et al. Derivatized dialdehyde starches, such as described in Japanese Kokai Tokkyo Koho JP 03,185,197, should also find application as useful materials for providing temporary wet strength. It is also expected that other temporary wet strength materials such as those described in U.S. Pat. No. 4,981,557; U.S. Pat. No. 5,008,344 and U.S. Pat. No. 5,085,736 to Bjorkquist would be of use in this invention. With respect to the classes and the types of wet strength resins listed, it should be understood that this listing is simply to provide examples and that this is neither meant to exclude other types of wet strength resins, nor is it meant to limit the scope of this invention.

Although wet strength agents as described above find particular advantage for use in connection with in this invention, other types of bonding agents can also be used to provide the necessary wet resiliency. They can be applied at the wet end or applied by spraying or printing, etc. after the web is formed or after it is dried.

As used herein, the wet:dry ratio is simply the ratio of the geometric mean wet tensile strength divided by the geometric mean dry tensile strength. The geometric mean tensile strength is the square root of the product of the machine direction tensile strength and the cross-machine direction tensile strength. Tensile strength is measured with an Instron tensile tester using a 3 inches jaw width, a 4 inches jaw span, and a crosshead speed of 10 inches per minute. Absorbent structures of this invention have a wet:dry ratio of 0.1 or greater, more specifically about 0.2 or greater, still more specifically about 0.35 or greater, and still more specifically about 0.5 or greater.

As used herein, "density" is determined by measuring the caliper of a single sheet as described below. Density is calculated by dividing the caliper by the basis weight of the sheet. The density of the absorbent structures of this invention is about 0.3 grams per cubic centimeter or greater, more specifically about 0.4 grams per cubic centimeter or greater, more specifically from about 0.45 to about 0.6 grams per cubic centimeter, and still more specifically from about 0.5 to about 0.65 grams per cubic centimeter.

When saturated with distilled water, the density of the absorbent structure of this invention can decrease about 20 percent or greater, more specifically about 40 percent or greater, still more specifically about 60 percent or greater, still more specifically about 80 percent or greater, and still more specifically from about 40 to about 80 percent.

As used herein, "caliper" is the thickness of the sheet measured using a EMVECO Model 200-A with the following specifications: pressure foot lowering speed 0.8 millimeter per second; surfaces of pressure foot and anvil must be parallel to within 0.001 millimeter; capability of repeated readings to be within 0.001 millimeter at zero setting or on the calibrated gage; a flat ground circular fixed face (anvil) of a size that is in contact with the whole area of the pressure foot in the zero position; capacity, 0–12.7 millimeter; sensitivity, 0.025 millimeter; load, 2.0 kiloPascals; anvil area, 2500 square millimeters; and anvil diameter, 56.4 millimeters. Single-ply samples are placed on the anvil in such a way that the pressure foot is at least ¼ inch away from the edges of the sample. The average of two readings is the caliper, expressed in inches. Caliper can be measured wet or dry.

When fully wetted or saturated with distilled water, the caliper of the absorbent structure of this invention can increase about 200 percent or greater, more specifically about 400 percent or greater, still more specifically about 600 percent or greater, and still more specifically from about 200 to about 600 percent.

The aqueous absorbent capacity of the absorbent structures of this invention can be about 4 grams of water per gram of fiber or greater, more specifically about 10 grams of water per gram of fiber or greater, more specifically about 20 grams of water per gram of fiber or greater, and still more specifically from about 10 to about 20 grams of water per gram of fiber. The aqueous absorbent capacity can be determined as set forth in U.S. Pat. No. 5,399,412 issued Mar. 21, 1995 to Sudall et al. entitled "Uncreped Through-dried Towels and Wipers having High Strength and Absorbency", which is hereby incorporated by reference.

As used herein, "Surface Depth" is defined as the characteristic maximum surface height difference caused by a repeating topographical pattern on a tissue surface, as measured by a noncontacting optical method described below. For a tissues surface marked by a drying or forming fabric, the surface depth is the characteristic height gap between the lowest and highest parts of a typical unit cell from the surface, as shown in FIGS. 1A and 1B. The concept employed is similar to the maximum peak-to-valley height parameter, $R_{max}$, as is known in the art of surface texture analysis and as taught in "Surface Texture Analysis: The Handbook" by Leigh Mummery (Hommelwerke GmbH, Muhlhausen, Germany, 1990 pp. 28–29). To obtain surface depth from a height profile containing up to 5 repeating structures, each of the repeating structures (unit cells) is considered separately to find the maximum peak-to-valley difference for that structure. Then the maximum of the up to 5 repeating structures on the profile is taken as the surface depth of that profile. Profiles should be selected along portions of the repeating surface structure with the greatest height variation. Multiple profiles should be considered, with each profile containing the same number of repeating structures for consistency. The average of the surface depth values from the various profiles is taken as a characteristic surface depth value for the structure.

The surface depth measurement employed here is intended to resolve structures of greater size than a single fiber diameter, so a spatial resolution of about 70 microns is desired (i.e., the height and width of pixels in a contour map or height map of the surface will be about 70 microns), whereas the z-direction (height) resolution should be on the order of 2 microns or better. If the profile shows macroscopic variation due to curvature of the sample rather than due to unit cell structures, a polynomial fit or other means should be applied to remove the effect of the large scale variation and to ensure that the peak-to-valley heights measured truly correspond to those of typical repeating structures on the surface.

The surface depth is preferably measured using a computer-controlled white-light field-shifted moire interferometer with a 38 mm. field of view. The principles of a useful implementation of such a system are described in Bieman et al. (L. Bieman, K. Harding and A. Boehnlein, "Absolute Measurement Using Field-Shifted Moire," SPIE Optical Conference Proceedings, Vol. 1614, pp. 259–264, 1991). A suitable commercial instrumenet for moire interferometry is the CADEYES® interferometer produced by Medar, Inc. (Farmington Hills, Mich.), constructed for a 38 mm. field of view (a field of view within the ragne of 37 to 39.5 mm. is adequate).

In the CADEYES moire interferometry system, each pixel in the CCD video image is said to belong to a moire fringe that is associated with a particular height range. The method of field-shifting, as described by Bieman et al. and as originally described in U.S. Pat. No. 5,069,548 issued Dec. 3, 1991 to Boehnlein, herein incorporated by reference, is used to identify the fringe number for each point in the video image (indicating to which fringe a point belongs). The fringe number is needed to determine the absolute height at the measurement point relative to a reference plane. A field-shifting technique (sometimes termed phase-shifting in the art) is also used for sub-fringe analysis (accurate determination of the height of the measurement point within the height range occupied by its fringe). These field-shifting methods coupled with a camera-based interferometry approach allows accurate and rapid absolute height measurement, permitting measurement to be made in spite of possible height discontinuities in the surface. The technique allows absolute height of each of the roughly 250,000 discrete points (pixels) on the sample surface to be obtained if suitable optics, video hardware, data acquisition equipment and software are used that incorporate the principles of moire interferometry with field-shifting. Each point measured has a resolution of approximately 1.5 microns in its height measurement.

The computerized interferometer system is used to acquire topographical data and then to generate a grayscale image of the topographical data, said image to be hereinafter called "the height map." The height map is displayed on a computer monitor, typically in 256 or more shades of gray and is quantitatively based on the topographical data obtained for the sample being measured. Again, the optical system should use a 38 mm.×38 mm. field of view. The resulting height map for the 38 mm. square measurement area should contain approximately 250,000 data points corresponding to approximately 500 pixels in both the horizontal and vertical directions of the displayed height map. The pixel dimensions of the height map are based on a 512×512 CCD camera which provides images of moire patterns on the sample which can be analyzed by computer software. Each pixel in the height map represents a height measurement at the corresponding x- and y- location on the sample. In the recommended system, each pixel has a width of approximately 70 microns. The z-direction height measurement must have a nominal accuracy of less than 2 microns and a z-direction of at least 1.5 mm. (For further background on the measurement method, see the CADEYES Product Guide, Medar, Inc., Farmington Hills, Mich., 1994 or other CADEYES manuals and publications of Medar, Inc.).

To measure surface depth, the operator should draw profile lines on the height map over characteristic repeating structures such as wire marks and then measure automatically or manually the surface depth of typical structures, using the definition of surface depth given above.

Additionally, the surface roughness paratmeter, $R_a$, can be measured. This widely-used parameter gives the mean absolute deviation of a profile from the least squares line passing through it. Rather than measure the roughness of a single profile, however, an area of the height map should be selected having 10,000 to 20,000 pixels, representing a region without obvious macroscopic curvature, and the mean absolute deviation of those points from the least-squares fit plan passing through these points should be determined and used as the roughness parameter. While this surface-area roughness parameter is labeled as $R_a$ in the commercial software for the CADEYES system, it must be recalled that an area-based measurement is being used rather than the profile line-based $R_a$ parameter commonly used in profilometry.

The moire interferometer system, once installed and factory calibrated to provide the accuracy and z-direction range stated above, can provide accurate topographical data for materials such as bath tissue. (Those skilled in the art may confirm the accuracy of factory calibration by performing measurements on surfaces with known dimensions). In performing a test, a sample of dry or wet tissue is palced flat on a surface lying aligned or nearly aligned with the measurement plane of the instrument and should be at such a height that both the lowest and highest regions of interest are within the measurement region of the instrument.

Once properly placed, data acquisition is initiated using the PC software and a height map of 250,000 data points is acquired and displayed, typically within 30 seconds from the time data acquisition was initiated. (Using the CADEYES system, the "contrast threshold level" for noise rejection is set to 1, providing some noise rejection without excessive rejection of data points). Data reduction and display are achieved using CADEYES software for PCs, which incorporates a customizable interface based on Microsoft Visual Basic Professional for Windows (version 3.0). The Visual Basic interface allows users to add custom analysis tools.

Once a 38 mm. square area of a tisuse surface has been measured topographically, characteristic structures are selected to yield two-dimensional height profiles extracted from straight lines drawn on the height map of the surface. These profiles should be flat (preferably adjusted by subtraction of the least-squares linear fit of the profile). Three to five of the repeating structures should be visible within the profile. The surface depth is then calculated as described above.

When the absorbent structures of this invention are fully wetted with distilled water, the Surface Depth can increase by about 300 percent or greater, more specifically by about 400 percent or greater, more specifically by about 500 percent or greater, and still more specifically by from about 300 percent to about 600 percent. This value will depend upon the 3-dimensionality of the structure prior to compression and its dry compressibility, since the Surface Depth of the wetted structure will tend to approach the initial Surface Depth of the dry structure.

BRIEF DESCRIPTION OF THE DRAWING

FIG. 3 is a schematic representation of a simple heated calender roll press useful for purposes of this invention.

DETAILED DESCRIPTION OF THE DRAWING

Figure 1:
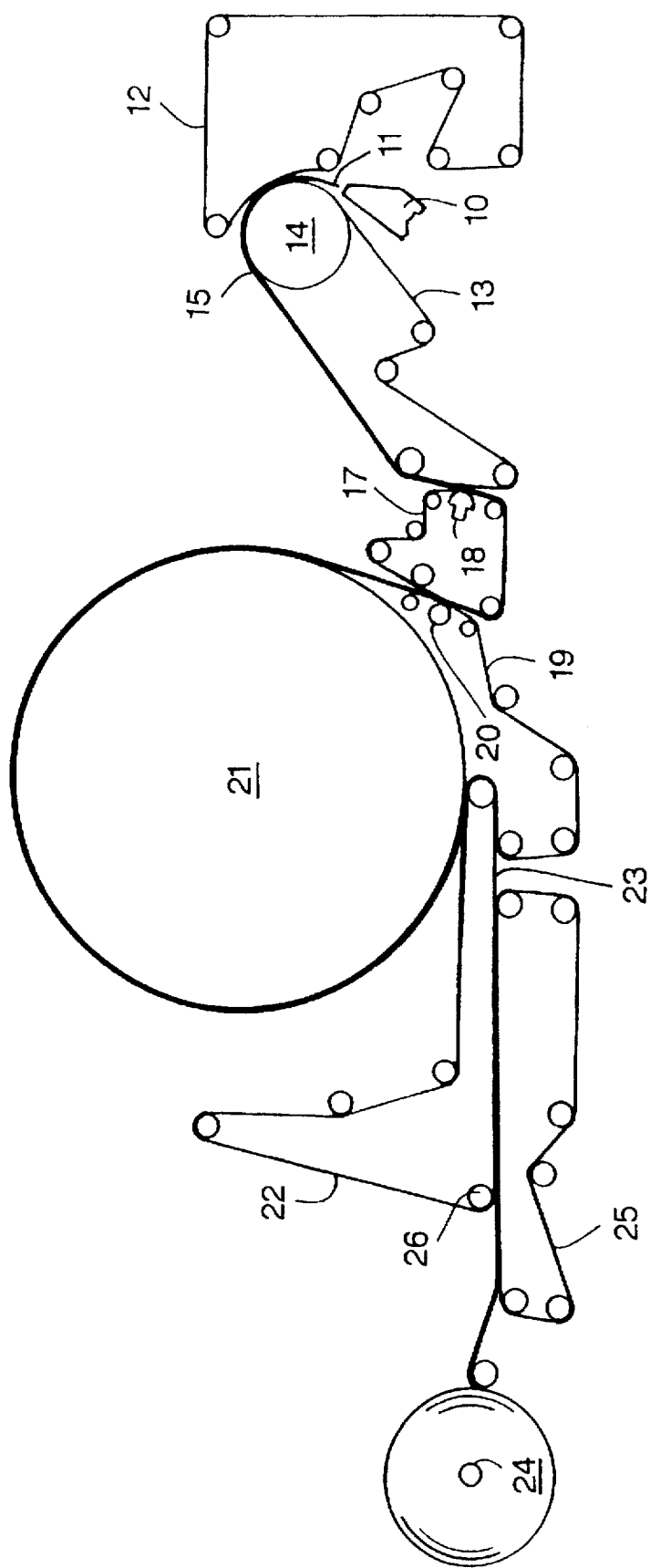
FIG. 1 is a schematic diagram of an uncreped through-dried papermaking process useful for making wet resilient absorbent structures of this invention.

Referring to FIG. 1, shown is a method for making throughdried paper sheets in accordance with this invention. (For simplicity, the various tensioning rolls schematically used to define the several fabric runs are shown but not numbered. It will be appreciated that variations from the apparatus and method illustrated in FIG. 1 can be made without departing from the scope of the invention). Shown is a twin wire former having a layered papermaking headbox 10 which injects or deposits a stream 11 of an aqueous suspension of papermaking fibers onto the forming fabric 13 which serves to support and carry the newly-formed wet web downstream in the process as the web is partially dewatered to a consistency of about 10 dry weight percent. Additional dewatering of the wet web can be carried out, such as by vacuum suction, while the wet web is supported by the forming fabric.

The wet web is then transferred from the forming fabric to a transfer fabric 17 traveling at a slower speed than the forming fabric in order to impart increased stretch into the web. Transfer is preferably carried out with the assistance of a vacuum shoe 18 such that the forming fabric and the transfer fabric converge and diverge simultaneously at the leading edge of the vacuum slot as described in copending application Ser. No. 08/330,166 filed Apr. 12, 1994 in the names of Engel et al.

The web is then transferred from the transfer fabric to the throughdrying fabric 19 with the aid of a vacuum transfer roll 20 or a vacuum transfer shoe, optionally again using a fixed gap transfer as previously described. The throughdrying fabric can be traveling at about the same speed or a different speed relative to the transfer fabric. If desired, the throughdrying fabric can be run at a slower speed to further enhance stretch. Transfer is preferably carried out with vacuum assistance to ensure deformation of the sheet to conform to the throughdrying fabric, thus yielding desired bulk and appearance. Suitable throughdrying fabrics include those having a three-dimensional contour as described in U.S. Pat. No. 5,429,686 issued Jul. 4, 1995 to Chiu et al. entitled "Apparatus For Making Soft Tissue Products", which is hereby incorporated by reference.

The level of vacuum used for the web transfers can be from about 3 to about 15 inches of mercury (75 to about 380 millimeters of mercury), preferably about 5 inches (125 millimeters) of mercury. The vacuum shoe (negative pressure) can be supplemented or replaced by the use of positive pressure from the opposite side of the web to blow the web onto the next fabric in addition to or as a replacement for sucking it onto the next fabric with vacuum. Also, a vacuum roll or rolls can be used to replace the vacuum shoe(s).

While supported by the throughdrying fabric, the web is final dried to a consistency of about 94 percent or greater by the throughdryer 21 and thereafter transferred to a carrier fabric 22. The dried basesheet 23 is transported to the reel 24 using carrier fabric 22 and an optional carrier fabric 25. An optional pressurized turning roll 26 can be used to facilitate transfer of the web from carrier fabric 22 to fabric 25. Suitable carrier fabrics for this purpose are Albany International 84M or 94M and Asten 959 or 937, all of which are relatively smooth fabrics having a fine pattern.

Figure 2:
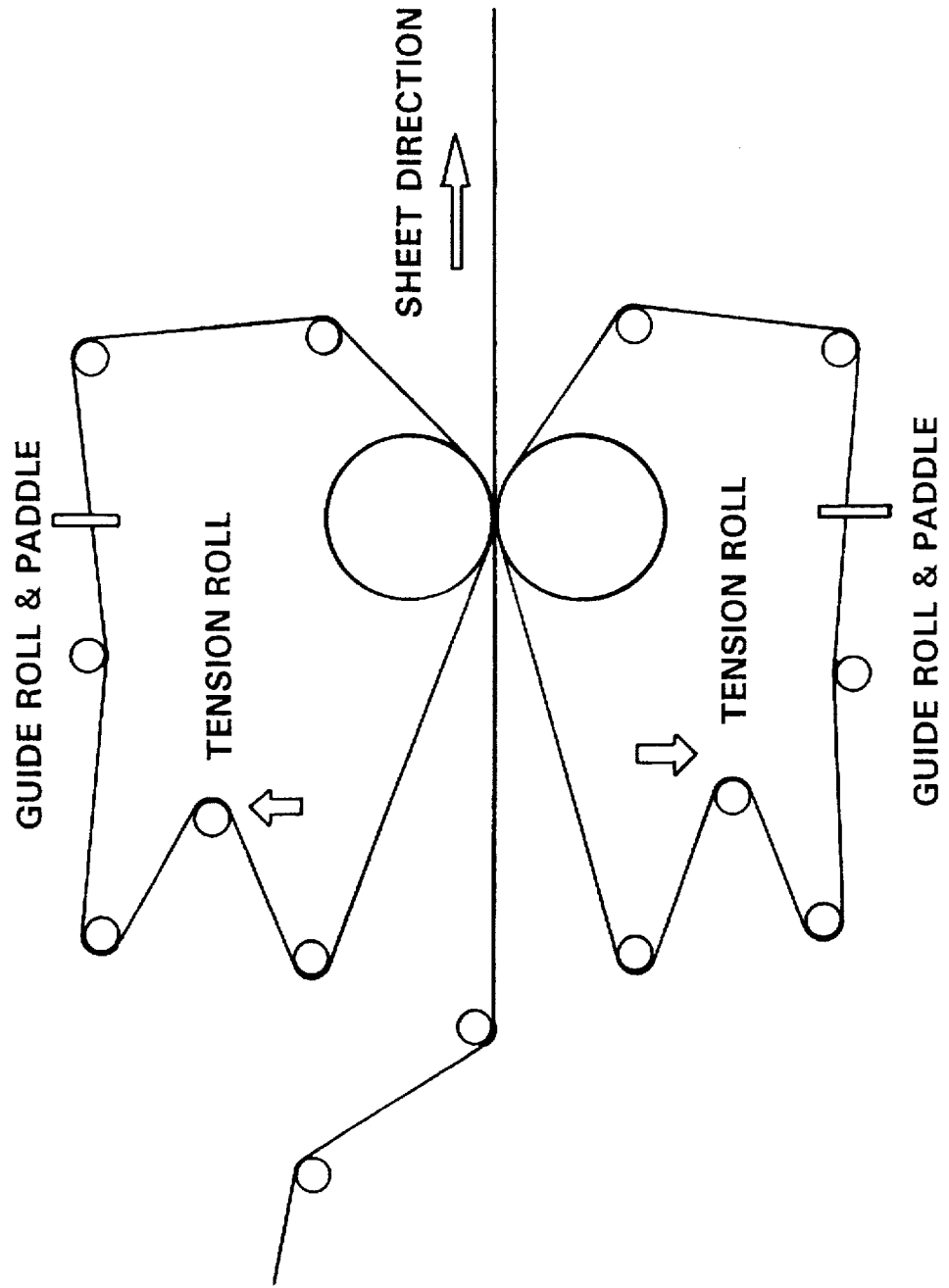
FIG. 2 is a schematic representation of a fabric calendering method useful for purposes of this invention.

FIG. 2 illustrates an alternative calendering method useful for purposes of this invention in which the sheet is calendered in a nip between two fabrics.

FIG. 3 is a schematic representation of a simple heated calender roll press useful for producing the materials of this invention.

Figure 4A:
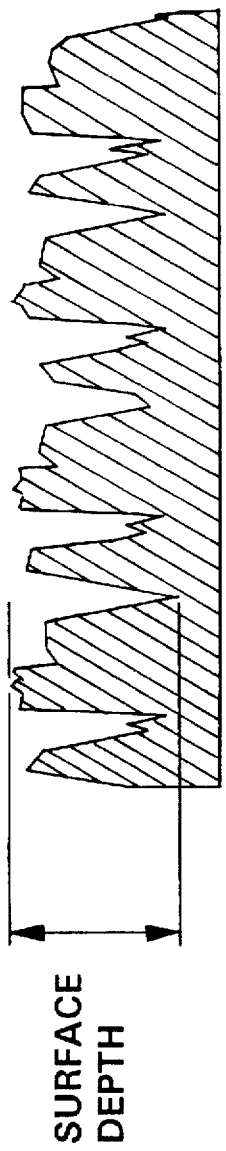
FIG. 4a is a schematic cross-sectional view of a tissue, illustrating the Surface Depth.
Figure 4B:
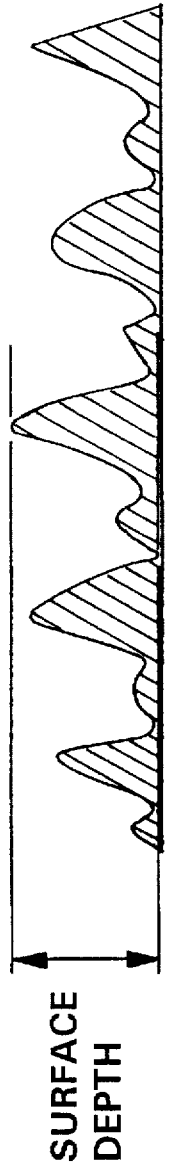
FIG. 4b is a schematic cross-sectional view of a tissue similar to FIG. 1a, also illustrating Surface Depth.

FIGS. 4a and 4b are discussed in connection with the Surface Depth.

EXAMPLES

In order to illustrate the invention, low density uncreped through-air-dried (UCTAD) sheets were produced as illustrated in FIG. 1 and then subjected to a variety of calendering conditions to densify the sheet. The sheets were then fully wetted and dried. The caliper before and after wetting was measured, as well as the machine direction (MD) and cross-machine direction (CD) tensile strengths before and after wetting.

In addition, several examples of heavy calendered uncreped tissue sheets were examined for Surface Depth before and after wetting the samples. Square samples were cut from existing calendered sheets and placed under a sample holder which restrains the edges of a 2-inch square but does not compress or modify the sample surface to be examined optically. The dry surface topography was then examined with the CADEYES 38 mm. field-of-view system. The dry sample was then spray moistened with room temperature (72° F.) deionized water until the sample was saturated. Spraying was completed in about 15 seconds. The sample was allowed to equilibriate for approximately 30 seconds, then it was lightly blotted with a paper towel and placed in the sample holder for CADEYES topography measurements. The sample was measured with the more textured side up (the fabric side, typically). Measurements of the wetted sample should be completed within about 3 minutes from the first moistening of the sample and preferably should be performed in a TAPPI-conditioned room.

The topographical data from the wetted sample is then reduced to provide characteristic Surface Depth values, which can be compared to the dry Surface Depth values. Care should be taken to ensure that the Surface Depth measurements reflect the topography of repeating structures on the surface and not of gross curvature or distortions in the sheet.

The results of the foregoing testing are summarized in TABLES 1 and 2 below:

TABLE 1

| Sample | Calendering | Dry Surface Depth, mm | Wet Surface Depth, mm | R$_a$ Dry mm | R$_a$ Wet, mm |
|---|---|---|---|---|---|
| 1-950517-12: UCTAD, 100% Spruce BCTMP 40 gsm, 20# Kymene/ton of fiber, 15% Rush Transfer, TAD Fabric 116-1. | 2500 psi, 65° C., 18 fpm | ca. 0.05 mm | 0.15 mm | <0.025 | 0.063 |
| 1-950517-9: UCTAD, 100% Spruce BCTMP, 60 gsm, 0# Kymene/ton of fiber, 15% Rush Transfer, TAD Fabric 116-1. | 1500 psi, 65° C., 36 fpm | <0.04 mm. | 0.16 mm | <=0.015 | 0.062 |
| 1-95017-10: UCTAD, 100% Spruce BCTMP, 60 gsm, 20# Kymene/ton of fiber, 15% Rush Transfer, TAD Fabric 116-1. | 1500 psi, | 0.05 mm | >0.3 mm | <=0.017 | 0.063 |
| 1-950516-6: UCTAD 100% Eucalyptus, 60 gsm, 20# Kymene/ton of fiber, 15% Rush Transfer, TAD Fabric 116-1. | 40 psi, 65° C., 36 fpm | <0.03 mm (Glossy) | 0.17–0.2 mm (the texture collapsed again upon drying. | NA | <0.055 |
| UCTAD 100% Spruce BCTMP 10# Kymene/ton of fiber | 400 psi 100 fpm | 0.1 | 0.35 | 0.016 | 0.075 |
| UCTAD 100% Spruce BCTMP 10# Kymene/ton of fiber | Uncal. | 0.35 | 0.55 | 0.11 | 0.13 |

TABLE 2

| Sample ID | Caliper As Is | Caliper After Wetting & Air Drying | MD Tensile As Is | MD Tensile Wet | CD Tensile As Is | CD Tensile Wet |
|---|---|---|---|---|---|---|
| Spruce BCTMP 80 gsm | 24.92 | 25.72 | 6.72 | 2.14 | 5.63 | 2.52 |
| Calendered 1500 psi | 4.07 | 19.77 | 6.85 | 1.72 | 5.87 | 1.45 |
| Spruce BCTMP 60 gsm | 20.51 | 21.16 | 4.26 | 1.97 | 3.95 | 1.53 |
| Calendered 1500 psi | 2.90 | 15.36 | 4.98 | 0.97 | 3.95 | 0.9 |
| Spruce BCTMP 40 gsm | 14.66 | 15.62 | 2.32 | 0.82 | 2.13 | 0.85 |
| Calendered 1500 psi | 2.12 | 10.18 | 2.73 | 0.4 | 2.39 | 0.44 |
| Eucalyptus 80 gsm | 25.57 | 25.74 | 3.36 | 1.58 | 2.91 | 1.13 |
| Calendered 1500 psi | 3.11 | 5.49 | 5.83 | 1.6 | 4.96 | 1.44 |
| Eucalyptus 60 gsm | 22.27 | 22.26 | 2.24 | 1.03 | 1.86 | 0.76 |
| Calendered 1500 psi | 2.51 | 5.33 | 4.09 | 0.93 | 2.83 | 0.68 |
| Eucalyptus 40 gsm | 13.01 | 13.27 | 1.14 | 0.5 | 1.05 | 0.39 |
| Calendered 1000 psi | 2.51 | 4.26 | 1.46 | 0.39 | 1.37 | 0.35 |

As illustrated by the foregoing data, the high density materials of this invention, upon being wetted, possess the ability to substantially return toward their initial state prior to being compressed.

It will be appreciated that the foregoing examples, given for purposes of illustration, are not to be construed as limiting the scope of this invention, which is defined by the following claims and all equivalents thereto.

We claim:

1. A method of making an absorbent structure comprising:
   (a) Forming a structure having a density of about 0.2 grams per cubic centimeter or less, said structure comprising wet-resilient fibers and having a wet:dry geometric mean tensile ratio of about 0.1 or greater; and
   (b) Compressing the structure to increase its density to about 0.3 grams per cubic centimeter or greater, wherein upon being saturated with water, the density decreases about 20 percent or greater.

2. The method of claim 1 wherein compression of the structure increases the density about 100 percent or greater.

3. The method of claim 1 wherein compression of the structure increases the density about 200 percent or greater.

4. The method of claim 1 wherein compression of the structure increases the density about 300 percent or greater.

5. The method of claim 1 wherein compression of the structure increases the density about 400 percent or greater.

6. A method of making an absorbent structure comprising:
   (a) forming an uncreped through-air-dried web comprising wet-resilient fibers and having a wet:dry geometric mean tensile ratio of about 0.1 or greater; and
   (b) calendering the web to increase its density to about 0.3 grams per cubic centimeter or greater, wherein upon being saturated with water, the density decreases about 20 percent or greater.

7. The method of claim 6 wherein the web is calendered at a pressure of from about 35 pounds per linear inch to about 1500 pounds per linear inch.

8. The method of claim 6 wherein the web is calendered at a pressure of about 50 pounds per linear inch to about 1200 pounds per linear inch.

9. The method of claim 6 wherein calendering increases the density about 200 percent or greater.

10. The method of claim 6 wherein calendering increases the density about 300 percent or greater.

11. The method of claim 6 wherein calendering increases the density about 400 percent or greater.

* * * * *